United States Patent [19]
Pershadsingh et al.

[11] Patent Number: 5,843,970
[45] Date of Patent: Dec. 1, 1998

[54] THIAZOLIDINE DERIVATIVES FOR THE TREATMENT OF HYPERTENSION

[76] Inventors: Harrihar A. Pershadsingh, 2812 Burger St., Bakersfield, Calif. 93305; Theodore W. Kurtz, 1251 Lattie La., Mill Valley, Calif. 94941

[21] Appl. No.: 725,327

[22] Filed: Jul. 8, 1991

Related U.S. Application Data

[63] Continuation-in-part of Ser. No. 421,102, Oct. 13, 1989, Pat. No. 5,053,420.

[51] Int. Cl.$^6$ ............................ A61K 31/44; A61K 31/42
[52] U.S. Cl. ............................................ 514/365; 514/342
[58] Field of Search .................................... 514/369, 342, 514/359, 376

[56] References Cited

U.S. PATENT DOCUMENTS

| | | | |
|---|---|---|---|
| 4,444,779 | 4/1984 | Kawamatsu et al. | 424/263 |
| 4,461,902 | 7/1984 | Kawamatsu et al. | 548/183 |
| 4,486,594 | 12/1984 | Kawamatsu et al. | 548/183 |
| 4,572,912 | 2/1986 | Yoshioka et al. | 514/369 |
| 4,582,839 | 4/1986 | Meguro et al. | 514/342 |
| 4,703,052 | 10/1987 | Eggler et al. | 514/337 |
| 4,725,610 | 2/1988 | Meguro et al. | 514/369 |
| 4,762,849 | 8/1988 | Grisar et al. | 514/369 |
| 4,775,687 | 10/1988 | Meguro et al. | 514/369 |
| 4,791,125 | 12/1988 | Clark | 514/365 |
| 4,798,835 | 1/1989 | Krupp et al. | 514/365 |
| 4,812,570 | 3/1989 | Meguro et al. | 546/280 |
| 4,880,824 | 11/1989 | Press et al. | 514/368 |
| 4,962,117 | 10/1990 | Young et al. | 514/365 |
| 5,002,953 | 3/1991 | Hindley | 514/275 |
| 5,063,240 | 11/1991 | Hindley | 514/369 |

FOREIGN PATENT DOCUMENTS

| | | |
|---|---|---|
| 277836 | 8/1988 | European Pat. Off. . |
| 56-71081 | 6/1981 | Japan . |

OTHER PUBLICATIONS

Kurtz, T.W., et al., "The Zucker Fatty Rat as a Genetic Model of Obesity and Hypertension," *Hypertension* 13:896–901 (1989).

Reaven, G.M., et al., "Attenuation of Fructose–Induced Hypertension in Rats by Exercise Training," *Hypertension* 12: 129–132 (1988).

Mondon, C.E. and Reaven, G.M., "Preliminary Report: Evidence of Abnormalities of Insulin Metabolism in Rats with Spontaneous Hypertension," *Metabolism* 37:303–305 (1988).

Hwang, I., et al., "Fructose–Induced Insulin Resistance and Hypertension in Rats," *Hypertension* 10: 512–516 (1987).

Tedde, R., et al., "Antihypertensive Effect of Insulin Reduction in Diabetic–Hypertensive Patients," *Amer. J. Hypertension* 2:163–170 (1989).

Hall, J.E., et al. "Does Chronic Hyperinsulinemia Cause Hypertension?" *Amer. J. Hypertension* 2:171–173 (1989).

Zavaroni, I., et al., "Risk Factors for Coronary Artery Disease in Healthy Persons with Hyperinsulinemia and Normal Glucose Tolerance," *N. Eng. J. Med.* 320:702–706 (1989).

Ferrannini, E., et al., "Insulin Resistance in Essential Hypertension," *N. Eng. J. Med.* 317:350–357 (1987).

Fuh, M., et al., "Abnormalities of Carbohydrate and Lipid Metabolism in Patients with Hypertension," *Arch. Intern. Med.* 147:1035–1038 (1987).

Reaven, G.M. and Hoffman, B.B., "Occasional Survey: A Role for Insulin in the Aetiology and Course of Hypertension?" *Lancet* pp. 435–436, Aug. 22, 1987.

Zavaroni, I., et al., "Evidence that Multiple Risk Factors for Coronary Artery Disease Exist in Persons with Abnormal Glucose Tolerance," *Amer. J. Med.* 83:609–612 (1987).

Manicardi, V., et al., "Evidence for an Association of High Blood Pressure and Hyperinsulinemia in Obese Man," *J. Clin. Endocrinol. Metab.* 62:1302–1304 (1986).

Lucas, C.P., et al., "Insulin and Blood Pressure in Obesity," *Hypertension* 7:702–706 (1985).

Dustan, H.P., "Mechanisms of Hypertension Associated with Obesity," *Ann. Intern. Med.* 98:860–864 (1983).

Reaven, G.M. and Hoffman, B.B., "Hypertension: A Disease of Carbohydrate and Lipoprotein Metabolism," *The Kidney* 29:19–23 (1988).

Foster, D.W., "Insulin Resistance—A Secret Killer?" *N. Eng. J. Med.* 320:733–734 (1989).

Reaven, G.M., "Banting Lecture: Role of Insulin Resistance in Human Disease," *Diabetes* 37:1595–1607 (1988).

Colca, J.R., et al., "Ciglitazone, a Hypoglycemic Agent: Early Effects on the Pancreatic Islets of Ob/Ob Mice," *Metabolism* 37:276–280 (1988).

Chang, A.Y., et al., "Ciglitazone, a New Hypoglycemic Agent," *Diabetes* 32:830–838 (1983).

Rocchini, A.P., et al., "The Effect of Weight Loss on the Sensitivity of Blood Pressure to Sodium in Obese Adolescents," *N. Eng. J. Med.* 321:580–585 (1989).

DeFronzo, R.A., "The Effect of Insulin on Renal Sodium Metabolism," *Diabetologia* 21:165–171 (1981).

Pershadsingh, H.A. and Kurtz, T.W., "Letter to:" *N. Eng. J. Med.* 318:383–384 (1988).

Pershadsingh, H.A. and McDonald, J.M., "Hormone–Receptor Coupling and the Molecular Mechanism of Insulin Action in the Adipocyte: A Paradigm for $Ca^{2+}$ Homeostasis in the Initiation of the Insulin–Induced Metabolic Cascade," *Cell Calcium* 5:111–130 (1984).

Klip, A., "Is Intracellular $Ca^{2+}$ Involved in Insulin Stimulation of Sugar Transport? Fact and Prejudice," *Canad. J. Biochem. Cell. Biol.* 62:1228–1236 (1984).

Sugiyama, T., et al., "The Elevation of the Cytoplasmic Calcium Ions in Vascular Smmoth Muscle Cells in SHR—Measurement of the Free Calcium Ions in Single Living Cells by Lasermicrofluorospectrometry," *Biochem. Biophys. Res. Comm.* 141:340–345 (1986).

*Primary Examiner*—Theodore J. Criares
*Attorney, Agent, or Firm*—Townsend and Townsend and Crew LLP

[57] ABSTRACT

This invention relates to a second medical use of thiazolidine compounds having anti-diabetic properties. These compounds are also of use for the control of essential hypertension.

1 Claim, No Drawings

THIAZOLIDINE DERIVATIVES FOR THE TREATMENT OF HYPERTENSION

The application is a Continuation-in-Part of U.S. application Ser. No. 07/421,102 filed Oct, 13, 1989 now U.S. Pat. No. 5,053,420.

BACKGROUND OF THE INVENTION

1. Field of the Invention

This invention relates to a second medical use of thiazolidine compounds having anti-diabetic properties. These compounds are also of use for the control of essential hypertension.

Hypertension of unknown etiology is termed essential hypertension. A relatively common disease state in people, this disease has been associated with the early onset of coronary disease, kidney failure and stroke. Essential hypertension is generally asymptomatic and has been termed a silent killer. It is believed to affect 60 million people in the United States.

Current pharmaceutical treatments for essential hypertension include diuretics, beta-blockers, angiotensin converting enzyme inhibitors and calcium antagonists. Currently available anti-hypertensive agents are not without side effects such as the elevation of blood lipids and glucose. The elevation of blood lipids and glucose by these agents has been suggested as a reason why anti-hypertensive agents have not demonstrated any benefit to patients being monitored in death rate studies.

While not wishing to be bound by theory, insulin levels are known to be high in individuals with hypertension. The association of carbohydrate metabolic abnormalities with hypertension has been suggested. There has been significant debate on the cause of essential hypertension, the mechanism and role of insulin or high levels of glucose on hypertension.

To date a causal relationship between insulin levels and hypertension has not been established. The biological mechanism of the pharmaceutical effects of the thiazolidine compounds of use in this invention is unknown. They are known to lower insulin, but the nature of this observation is unknown. It is unclear whether the insulin reduction associated with these drugs is directly or indirectly related to pancreas secretion, the peripheral cells or both.

To our knowledge no one has demonstrated a lowering of hypertension in non-obese, non-diabetic individuals by treatment with insulin lowering drug therapy. The discovery of a new use for this widely studied class of drugs will provide a new therapeutic approach for essential hypertension.

SUMMARY OF THE INVENTION

The present invention provides methods for the control of hypertension and attendant cardiovascular conditions by effective dosages of thiazolidine derivatives.

These compounds conform to the following structural formula I:

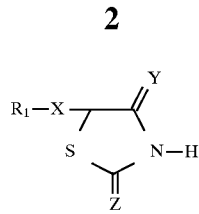

where variable ring substituents are defined below.

X is a lower alkylidene or a bond; or —HC=CH—;

Y is oxo or imino;

Z is oxo or imino; and $R_1$ is a structurally diverse variable comprised of the several compositions detailed as follows.

$R_1$ may be an aromatic carbocyclic or aromatic heterocyclic or substituted benzyl with X as a lower alkylidene. More particularly, $R_1$ may be of the formula IIa

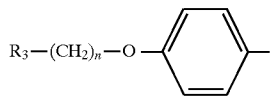

where $R_3$ is of the formula IIb.

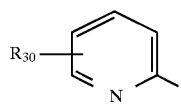

where $R_{30}$ is a lower alkyl of 1–4 carbons; or $R_3$ is of the formula IIc

where $R_{31}$ is hydrogen of lower alkyl of 1–4 carbons and the cyclohexane ring may be optionally substituted at any available methylene with single oxo or hydroxy; or $R_3$ is of the formula IId

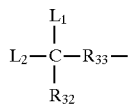

wherein $R_{32}$ is alkyl, cycloalkyl, phenylalkyl, phenyl, a five-or six-membered heterocyclic group including one or two hetero-atoms selected from the group consisting of nitrogen, oxygen and sulfur, or a group of the formula IIe

where $R_{34}$ and $R_{35}$ are the same or different and each is lower alkyl or $R_{34}$ and $R_{35}$ are combined to each other either directly or as interrupted by a hetero-atom selected from the group consisting of nitrogen, oxygen and sulfur to form a five- or six-membered ring as taken together with the nitrogen atom adjacent to $R_{34}$ and $R_{35}$; $R_{33}$ is a bond or a lower alkylidene group, $L_1$ and $L_2$ may be the same or different and each is a lower alkyl or $L_1$ and $L_2$ are combined to each other to form an alkylidene group, provided that when $R_{32}$ is other than alkyl, $L_1$ and $L_2$ may further be hydrogen, respectively.

Examples of compounds comprising thiazolidines derivatized with groups IIa, IIb, IIc, IId and IIe are:

5-(4-[2-(5-ethyl-2-pyridyl)ethoxy]benzyl)-2,4-thiazolidine dione;

5-[4-(1-methylcyclohexylmethoxybenzyl]thiazolidine dione, commonly called ciglitazone;

5-[4-(o-3-hydroxy-1-methyl-r-1-cyclohexylmethoxy)
benzyl]-thiazolidine-2,4-dione;

5-(4-[2-(4-methyl-5-thiazolyl)ethoxy]benzyl)
thiazolidine-2,4-dione; and 5-(4-[2-(4-methyl-5-pyridyl)ethoxy]benzyl]tiazolidine-2,
4-dione.

The thiazolidine derivative may further be selected from compounds where X is methylene and $R_1$ is of the formula IV

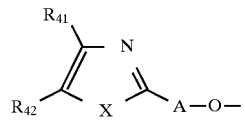

wherein X is an oxygen or sulfur atom, $R_{41}$ and $R_{42}$ are each independently hydrogen or a hydrocarbon residue which may optionally be substituted and $R_{41}$ and $R_{42}$ may jointly, together with the oxazole or thiazole ring, form a condensed ring and A is a lower alkylene group. Examples include:

5-(4-[2-(5-methyl-4-phenyl-2-oxazoyl)ethoxy]benzyl)-2,
4-thiazolidinedione; and, 5-[4-(4-phenyl-2-thiazolylmethoxy)benzyl]-2,4-
thiazolidinedione.

The thiazolidine may further be selected from compounds where X is methylene or —HC=CH— and $R_1$ is of formula V

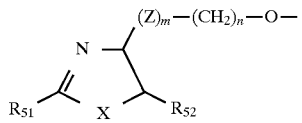

wherein $R_{51}$ is hydrogen or a hydrocarbon residue or heterocyclic residue which may each be substituted; $R_{52}$ is hydrogen or a lower alkyl group which may be substituted by hydroxyl group; X is an oxygen or sulfur atom; Z is a hydroxylated methylene or carbonyl; m is 0 or 1; n is an integer of 1 to 3; and pharmaceutically acceptable salts. Examples include:

5-[4-(2-phenyl-4-oxazolylmethoxy)benzyl]-2,4-
thiazolidinedione;

5-[4-(5-methyl-2-phenyl-4-oxazolylmethoxy)benzyl]-2,
4-thiazolidinedione; and, 5-(4-[2-(5-bromomethyl-2-phenyl-4-oxazolyl)ethoxy]
benzyl)-2,4-thiazolidinedione.

The thiazolidine derivative may be further selected from compounds where X is methylene and $R_1$ is of formula VI

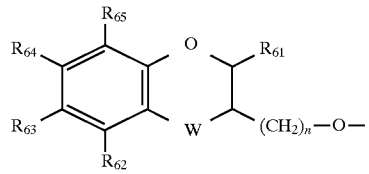

wherein $R_{61}$ and $R_{62}$ are the same or different and each represents a hydrogen atom or a $(C_1-C_5)$ alkyl group; $R_{63}$ represents a hydrogen atom, a $(C_1-C_6)$ aliphatic acyl group, an alicyclic acyl group, an aromatic acyl group, a heterocyclic acyl group, an araliphatic acyl group, a $(C_1-C_6$ alkoxy) carbonyl group or an aralkyloxycarbonyl group; $R_{64}$ and $R_{65}$ are the same or different and each represents a hydrogen atom, a $(C_1-C_5)$ alkyl group or a $(C_1-C_5)$ alkoxy group, or $R_{64}$ and $R_{65}$ together represent a $(C_1-C_4)$ alkylenedioxy group;

W represents the —$CH_2$—, >CO or >CH—O—$R_{66}$ group (in which $R_{66}$ represents any one of the atoms or groups defined for $R_{63}$ and may be the same as or different from $R_{63}$.

Examples of such compounds include:

5-[4-(6-fluoro-2-methylchroman-2-yl methoxy)benzyl]
thiazolidine-2,4-dione;

5-[4-6-fluoro-2-methyl-4-oxochroman-2yl methoxy)
benzyl]thiazolidine-2,4-dione;

5-[4-(6-acetyl-7-hydroxy-2,8-dimethyl-4-oxochroman-
2-yl methoxy)benzyl]thiazolidine-2,4-dione; and, 5-[4-(2,5,7-trimethylchroman-2-yl methoxy)benzyl]
thiazolidine-2,4-dione.

The thiazolidine derivative may be further selected from compounds where X is methylene and $R_1$ is of formula VII

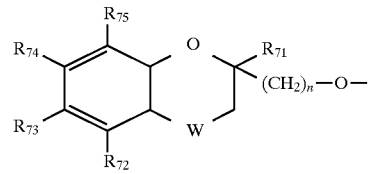

wherein: $R_{71}$ represents a hydrogen atom, a $(C_1-C_{25})$ alkyl group, a $(C_3-C_{10})$ cycloalkyl group or a substituted $(C_3-C_{10})$ cycloalkyl group having at least one $(C_1-C_6)$ alkyl substituent; $R_{72}$, $R_{74}$ and $R_{75}$ are the same or different and each represents: a hydrogen atom; a $(C_1-C_{25})$ alkyl group; a substituted $(C1-C_{26})$ having at least one of substituents (a); an aralkyl group; a $(C_3-C_{10})$ cycloalkyl group; a substituted $(C_3-C_{10})$ cycloalkyl group having at least one $(C_1-C_6)$ alkyl substituent; and aryl group; a halogen atom; a hydroxy group; a protected hydroxy group in which the protecting group is selected from substituents (b); a $(C_1-C_7)$ alkanoyl group; a substituted $(C_2-C_7)$ alkanoyl group having at least one of substituents (c); an arylcarbonyl group; a cycloalkylcarbonyl group in which the cycloalkyl part is $(C_3-C_{10})$; a substituted cycloalkylcarbonyl group in which the cycloalkyl part is $(C_3-C_{10})$ and has at least one $(C_1-C_6)$ alkyl substituent; a carboxy group; a $(C_2-C_7)$ alkoxycarbonyl group; an aryloxycarbonyl group; and aralkyloxycarbonyl group; a nitro group; a group of formula VIIb

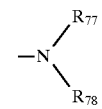

in which $R_{77}$ and $R_{78}$ are the same or different and each represents a hydrogen atom, a $(C_1-C_6)$ alkyl group, an aralkyl group, a $(C_3-C_{10})$ cycloalkyl group, an aryl group, a $(C_1-C_7)$ alkanoyl group, an aralkanoyl group, an arylcarbonyl group or a $(C_2-C_7)$ alkoxycarbonyl group, or $R_{77}$ and $R_{78}$, together with the nitrogen atom to which they are attached, form a nitrogen-containing heterocyclic group having from 5 to 10 ring atoms, of which one is said nitrogen atom and from 0 to 3 are additional nitrogen and/or oxygen and/or sulphur hetero-atoms. or a group of formula VIIc

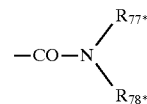

in which $R_{77*}$ and $R_{78*}$ are the same or different and each represents a hydrogen atom, a $(C_1-C_6)$ alkyl group, an aralkyl group, a $(C_3-C_{10})$ cycloalkyl group or an aryl group or $R_{77}$ and $R_{78}$, together with the nitrogen atom to which they are attached, form a nitrogen-containing heterocyclic group having from 5 to 10 ring atoms, of which one is said nitrogen atom and from 0 to 3 are independently additional nitrogen or oxygen or sulphur hetero-atoms; $R_{73}$ represents a hydrogen atom, a ($C_1$–$C_{25}$) alkyl group, a substituted ($C_1$–$C_{25}$) alkyl group having at least one of substituents (a), an aralkyl group, a ($C_3$–$C_{10}$) cycloalkyl group, a substituted ($C_3$–$C_{10}$) cycloalkyl group having at least one ($C_1$–$C_6$) alkyl substituent, an aryl group, a halogen atom, a ($C_1$–$C_7$) alkanoyl group, a substituted ($C_2$–$C_7$) alkanoyl group having at least one of substituents (c), an arylcarbonyl group, a cycloalkylcarbonyl group in which the cycloalkyl pat is ($C_3$–$C_1$), a substituted cycloalkylcarbonyl group in which the cycloalkyl part is ($C_3$–$C_{10}$) and has at least one ($C_1$–$C_6$) alkyl substituent, a carboxy group, a ($C_2$–$C_7$) alkoxycarbonyl group, an aryloxycarbonyl group, an aralkyloxycarbonyl group, a nitro group, a group of formula VIIb, as defined above, or a group of formula VIIc, as defined above; or $R_{73}$ represents a hydroxy group or a protected hydroxy group in which the protecting group is selected from substituents (b), provided that at least one of $R_{72}$, $R_{74}$ and $R_{75}$ represents a substituted alkyl group having at least one of substituents (a), a halogen atom, a hydroxy group, a substituted alkoxy group having at least one of substituents (c), a ($C_1$–$C_7$) alkanoyloxy group, a substituted ($C_2$–$C_7$) alkanoyloxy group having at least one of substituents (c), an arylcarbonyloxy group, a sulphoxy group, a ($C_1$–$C_7$) alkanoyl group, a substituted ($C_2$–$C_7$) alkanoyl group having at least one of substituents (c), a cycloalkylcarbonyl group in which the cycloalkyl part is, a substituted cycloalkylcarbonyl group in which the cycloalkyl part is ($C_3$–$C_{10}$) and has at least one ($C_1$–$C_8$) alkyl substituent, an arylcarbonyl group, a carboxy group, a ($C_2$–$C_7$) alkoxycarbonyl group, an aryloxycarbonyl group, an aralkyloxycarbonyl group, a nitro group, a group of formula VIIb, as defined above, or a group of formula VIIc, as defined above, Ar represents a divalent aromatic carbocyclic group or a divalent aromatic heterocyclic group; W represents a methylene group, a carbonyl group, a group of formula >CH—OY in which Y represents a hydrogen atom, a ($C_1$–$C_7$) alkanoyl group or an arylcarbonyl group, or a group of formula >C=N—OV in which V represents a hydrogen atom, a ($C_1$–$C_6$) alkyl group, a substituted ($C_1$–$C_6$) alkyl group having at least one of substituents (c), a ($C_1$–$_7$) alkanoyl group or an arylcarbonyl group; U represents a single bond or a methylene group;

or, when W represents a carbonyl group or said group of formula >C=N—OV, U, $R_{71}$ and the carbon atom to which $R_{71}$ is attached may together represent a group of formula —CH=C<; or when W represents a carbonyl group or said group of formula >C=N—OV, U, $R_{71}$ and the carbon atom to which $R_{71}$ is attached may together represent a group of formula —CH=C<; or W-U may represent a carbon-carbon double bond; and n represents an integer from 1 to 10; said aralkyl groups have an alkyl portion containing from 1 to 6 carbon atoms and an aryl portion as defined below, the alkyl portion being unsubstituted or having at least one of substituents (c); substituents (a):

hydroxy groups; protected hydroxy groups in which the protecting group is selected from substituents (b); ($C_1$–$C_7$) aliphatic carboxylic acyl groups; ($C_2$–$C_7$) aliphatic carboxylic acyl groups having at least one of substituents (c); arylcarbonyl groups; cycloalkylcarbonyl groups in which the cycloalkyl part is ($C_3$–$C_{10}$); substituted cycloalkylcarbonyl groups in which the cycloalkyl part is ($C_3$–$C_{10}$) and having at least one ($C_1$–$C_6$) alkyl substituent; carboxy groups; ($C_2$–$C_7$) alkoxycarbonyl groups; aryloxycarbonyl groups; aralkyloxycarbonyl groups; hydroxyimino groups; protected hydroxyimino groups in which the protecting group is selected from substituents (b); groups of formula VIIb, as defined above; and groups of formula VIIc, as defined above; substituents (b):

($C_1$–$C_6$) alkyl groups, substituted ($C_1$–$C_6$) alkyl groups having at least one of substituents (c), ($C_1$–$C_7$) aliphatic carboxylic acyl groups, substituted ($C_2$–$C_7$) aliphatic carboxylic acyl groups having at least one of substituents (c), arylcarbonyl groups, ($C_2$–$C_7$) alkoxycarbonyl groups, aryloxycarbonyl groups, groups of formula (VIIc), as defined above and sulpho groups; substituents (c):

carboxy groups, ($C_2$–$C_7$) alkoxycarbonyl groups and aryl groups;

said aryl groups and the aryl parts of said aralkyl, arylcarbonyl, aryloxycarbonyl, aralkyloxycarbonyl and divalent aromatic groups being ($C_6$–$C_{14}$) carbocyclic aryl groups which are unsubstituted or have at least one of substituents (d);

said heterocyclic groups, heterocyclic parts of said heterocyclic acyl and acyloxy groups and said divalent heterocyclic aromatic groups have from 5 to 14 ring atoms, of which from 1 to 5 are independently nitrogen, oxygen or sulphur hetero-atoms, said heterocyclic groups being unsubstituted or having at least one substituent selected from substituents (d) and substituents (e); substituents (d):

($C_1$–$C_6$) alkyl groups, ($C_1$–$C_6$) alkoxy groups, hydroxy groups, sulphoxy groups, halogen atoms, nitro groups, groups of formula (II), as defined above, ($C_1$–$C_7$) aliphatic carboxylic acyl groups, ($C_7$–$C_{11}$) arylcarbonyloxy groups in which the aryl part is unsubstituted or has at least one substituent selected from ($C_1$–$C_6$) alkyl groups, ($C_1$–$C_6$) alkoxy groups and halogen atoms; substituents (e):

aryl groups and oxygen atoms. Examples of compounds containing VII are

5-[4-(6-hydroxy-2,5,7,8-tetramethylchroman-2-yl methoxy)benzyl]thiazolidine-2,4-dione.

5-[4-(6-hydroxy-5,7,8-trimethylchroman-2-yl methoxy)benzyl]thiazolidine-2,4-dione.

5-[4-6-hydroxy-5,7-diisopropyl-2-methylchroman-2-yl methoxy)benzyl]thiazolidine-2,4-dione.

The thiazolidine derivative may further be selected from compounds where X is methylene and $R_1$ is of formula VIII

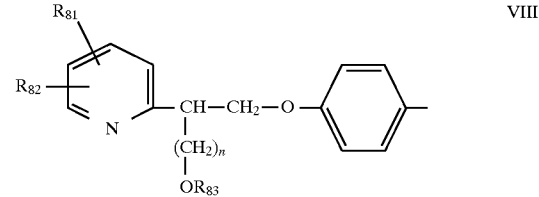

wherein $R_{81}$ and $R_{82}$ are the same or different and each represent hydrogen or a lower alkyl group; $R_{83}$ is hydrogen or acyl group; n is 0 or 1. Examples include:

5-(4-[2-(5-ethyl-2-pyridyl)-2-hydroxyethoxy]benzyl)-2, 4-thiazolidinedione; and, 5-(4-[2-hydroxy-2-(6-methyl-2-pyridyl)ethoxy]benzyl)-2,4-thiazolidinedione.

The thiazolidine dione may be further selected from compounds wherein X is a bond and $R_1$ is of formula where n is ann integer of 3 to 6.

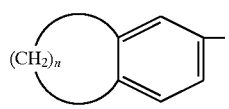

IX

Examples include:
5-(5,6,7,8-tetrahydro-2-naphthyl)thiazolidine-2,4-dione; and
5-(5-indanyl)thiazolidine-2,4-dione.

The thiazolidinedione may be further selected from compounds wherein Y and Z are oxo and $R_1$ is selected from compounds of the formula XI

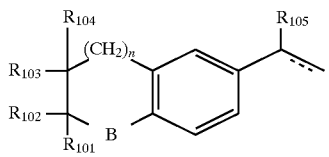

XI wherein the broken line is a bond or no bond, n is zero, 1 or 2; B is O,S, >S=O, >S(=O)$_2$; $R_{105}$ is H, $CH_3$, or $C_2H_5$; when taken separately, $R_{101}$ is H, ($C_5$–$C_7$) cycloalkyl, ($C_6$–$C_6$) methyl-substituted cycloalkyl, pyridyl, thienyl, furyl, naphthyl, p-biphenylyl, tetrahydrofuranyl, tetrahydrothienyl, tetrahydropyranyl, $C_6H_4W_2$ or alk-$W_1$ and alk is ($C_1$–$C_6$) alkylene, ethylidene or isopropylidene; $W_1$ is H, OH, ($C_1$–$C_4$) alkoxy, ($C_1$–$C_4$) thioalkyl, pyridyl, furyl, thienyl, tetrahydrofuryl, tetrahydrothienyl, naphthyl, ($C_5$–$C_7$) cycyloalkyl or $C_6H_4W_2$ and $W_2$ is H, OH, F, Cl, Br, ($C_1$–$C_4$) alkyl, ($C_1$–$C_4$) alkoxy or ($C_1$–$C_4$) thioalkyl; $R_{102}$ is H or $CH_3$, $R_{103}$ is H, ($C_1$–$C_6$) alkyl, $C_6H_4W_2$ or benzyl; and $R_{104}$ is H; when $R_{101}$ and $R_{102}$ are taken together they form ($C_4$–$C_6$) alkylene and $R_{103}$ and $R_{104}$ are each H; when $R_{103}$ and $R_{104}$ are taken together they form ($C_4$–$C_6$) alkylene and $R_{101}$ and $R_{102}$ are each H; and when $R_{102}$ and $R_{103}$ are taken together they are ($C_3$–$C_4$) alkylene and $R_{101}$ and $R_{104}$ are each H.

Examples include 5-[(2-benzyl-2,3-dihydrobenzofuran-5-yl)methyl]thiazolidine-2,4-dione and 5-[(2-benzyl-3,4-dihydro-2H-benzopyran-6-yl)methyl]thiazolidine-2,4-dione or a pharmaceutically acceptable salts thereof.

Definitions

Thiazolidine refers to an organic compound containing a derivatized thiazole ring system.

Carbocyclic describes a homocyclic ring compound in which all the ring atoms are carbon, e.g., benzene.

Heterocyclic refers to a ring compound having atoms other than carbon in its nucleus, e.g, pyrrole or thiophene.

Alkylidene, $C_nH_{2n}$, refers to a divalent organic radical derived from an aliphatic hydrocarbon, e.g., ethylidene in which two H atoms are taken from the same C atom.

Oxo is a prefix indicating the =O group as in aldehydes and 2-oxopropanoic acid.

Imino is a prefix indicating the =NH group attached to one or two carbon atoms; as =C:NH or —C—NH—C—.

Benzyl or phenylmethyl is an aryl radical derived from toluene.

Alkyl, $C_nH_{2n-L}$—, refers to a monovalent radical derived from an aliphatic hydrocarbon and designated by the number od carbon atoms, e.g., methyl, ethyl, propyl, etc.

Cycloalkyl is the generic name for radicals derived from cycloalkanes, e.g., cyclohexyl.

Phenyl refers to the radical $C_6H_5$— from benzene.

Methylene refers to the groups —$CH_2$— and =$CH_2$.

Oxazole refers to a liquid with formula $C_3H_{30}N$.

Thiazole is a heterocyclic, colorless liquid of formula $C_3H_3NS$.

Alicyclic refers to the group of cyclic organic compounds derived from the corresponding aliphatic compounds by ring formation and having a saturated ring such as the cyclopar-affins.

Acyl refers to an organic radical derived from an organic acid by removal of the hydroxyl group; e.g., R—C(O)— is the acyl radical of R-COOH. They are named by number of carbons; formyl, acetyl, propynyl, etc.

Alkoxy designates an alkyl radical attached to a nucleus through an oxygen, e.g., methoxy.

Aryl is an organic radical derived from an aromatic hydrocarbon by removal of one hydrogen, e.g., phenyl from benzene.

Alkylene is an alkene radical, $C_nH_{2n-1}$, as in ethylene.

Dioxy is a suffix indicating a —O—R—O— radical, where R is a bivalent radical such as carbonyldioxy, —O—CO—O—.

Alkylcarboxy designates a radical of the general formula R—C—, where R is an alkyl group.

Aralkyl is an arylated alkyl or a radical in which an alkyl H atom is substituted by an aryl group.

Carboxy or carboxyl is a prefix indicating the acidic group —COOH.

Sulfo is a prefix designating the sulfonic acid group, —$SO_3H$ or the presence of divalent sulfur.

Nitro is a prefix denoting the radical —$NO_2$.

Halo is a prefix indicating the presence of a halogen, e.g., fluoro, chloro, bromo, etc.

Protecting group here refers to any chemical group bonded to a functional group so as to eliminate its reactivity for a particular process.

Unless otherwise stated all carbon numbers ($C_x$–$C_y$) are inclusive. Where two carbon containing moieties are provided, such as alkylcarboxy of 1–7 carbons, the carboxy is included as a carbon of the 1–7. Thus, both formyl and hexylcarbonyl are embraced by the term alkoxy of 1–7 carbons.

Where asymmetric carbon atoms are present, all stereoisomeric forms are intended.

DETAILED DESCRIPTION

This invention provides for a pharmaceutical and method for controlling essential hypertension. The active ingredient of the pharmaceutical are well-known compounds and are generally described as 5'-Aryl Substituted thiazolidine derivatives. These compounds are known to be useful for the treatment of diabetes.

The compounds generally fall into the family of compounds of formula I which is then subdivided into several genera. Unless otherwise limited the symbols are as previously defined. The following details general guidance for the organic synthesis of the compounds of formula I.

A. Synthesis of Thiazolidine Ring and Substituents

Compounds having the general structural formula:

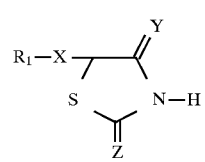

I can be synthesized by a variety of methods depending on the availability of starting compounds. The parent heterocyclic ring structure of formula I can be synthesized by the following reaction scheme which is found in the method of Kawamatsu, U.S. Pat. No. 4,486,594, and incorporated by reference herein.

1)

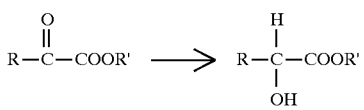

2)

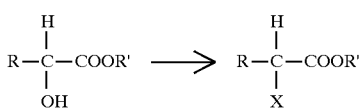

3)

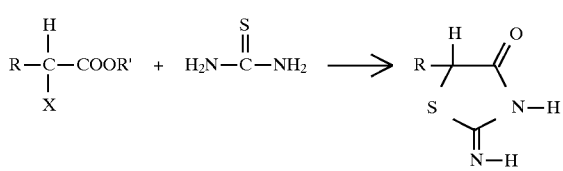

4)

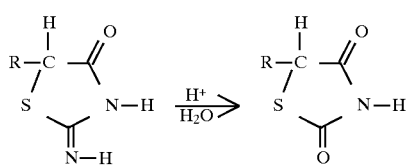

R represents any of the substituents of $R_1$; R' can be hydrogen, alkyl or aralkyl and X stands for a group to be eliminated.

Reaction 3) above yields a product where substituent Z from general formula (I) is imino. Therefore, reaction 4) is optional depending on the product desired.

Where it is desired to have substituent Y from general formula (I) to be an imino group, the following modifications can be used:

Start with a compound of the formula:

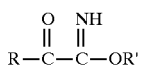

and proceed through steps 1) through 4) above.

Alternatively one may follow the method of Yoshioka et al., U.S. Pat. No. 4,572,912, which is incorporated by reference herein. To synthesize the thiazolidine ring begin with a compound of formula:

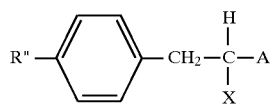

where substituent R" is any of the $R_1$ substituents of formula I (preferably the substituent represented by formula VI), where X is a halogen and where A is a cyano group. There is produced an imino substituent at the carbon at position 4 of the ring and where A is a carboxy, alkoxycarbonyl, an oxygen substitution will be effected at position 4 of the ring. Compound 3 can be reacted with thiourea in a reaction analogous to reaction 3) above to yield the following:

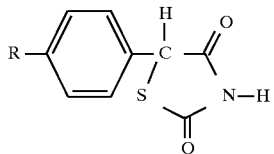

Details of the steps for the synthesis of the general compounds illustrated above will vary according to the nature of the $R_1$ groups in the general formula of I. In some instances blocking groups will need to be present in order to prevent unwanted side reactions. At times the nature, pH, and temperature of solvent mixtures may be variable for the same reason, but the following general conditions will apply to the synthetic scheme illustrated in reactions 1) through 4) above.

Reaction 1) is the reduction of the keto acid to the corresponding secondary alcohol. The reductant might be lithium aluminum hydride or sodium bis(2-methoxyethoxy) aluminum hydride. This reaction is preferably conducted in the presence of some solvent, the nature of which is not critical, provided that it does not interfere with the reaction. Suitable solvents include ethers, aromatic hydrocarbons and aliphatic hydrocarbons. It is preferable to use a ratio of reductant to keto acid of from one to two moles reductant per mole of keto acid. The reaction is generally carried out at 10° to 100° C. for a period from ten minutes to twenty hours.

Reaction 2) can be either a halogenation or sulfonylation of the product of reaction 1).

Halogenation is carried out by reacting a halogenating agent such as phosphorus tribromide, thionyl chloride or phosphorus oxychloride with the product of 1) in the presence or absence of a solvent such as dichloromethane or chloroform. The reaction is preferably conducted at an elevated temperature, for example 20° to 100° C.

Sulfonylation of the product of reaction 1) can be conducted by reacting the compound with sulfonylating agent, e.g. mesyl chloride, tosyl chloride or benzenesulfonyl chloride at 0° to 60° in a suitable solvent, e.g. benzene, ethyl acetate, dichloromethane or chloroform in the presence of a base such as pyridine or triethylamine.

The reaction of the compound formed in 2) is then allowed to react with thiourea usually in a solvent exemplified by alcohols, ethers, acetone, dimethylformamide, dimethylsulfoxide or sulfolane. The amount of thiourea is preferably 1–2 moles per mole of reaction 2) product. The reaction temperature is preferably 60° to 130° C.

If desired the compound of reaction 3) can then be hydrolyzed by heating in a suitable solvent such as sulfolane in the presence of water and a mineral acid. The acid is added in a proportion of preferably 0.2 to 3.0 equivalents per equivalent of reaction 3) product. Water is normally in large excess. Heating time ranges from 2–10 hours.

The object-compound of formula I can be isolated and purified by a conventional means such as concentration, solvent extraction, recrystallization, chromatography or the like. The object compound which may be an acid compound may be converted to a salt with, for example, alkali metal, alkaline earth metals, or organic bases such as sodium, potassium, calcium, amines and the like.

An alternative methodology for the formation of the starting compound (I) starts with a compound of R-OH where R corresponds to the $R_1$ of formula I absent an aryl moiety and are preferably compounds of formula IV. The alcohol is reacted with p-nitrofluorobenzene as illustrated below according to the method of Meguro et al., U.S. Pat. No. 4,775,687.

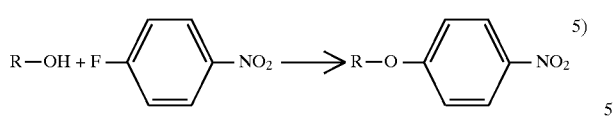

This reaction serves the advantage of allowing the aryl group to be added synthetically if it is not available in the $R_1$ moiety of formula I. Following the formation of the product of reaction 5), the following successive steps are taken:

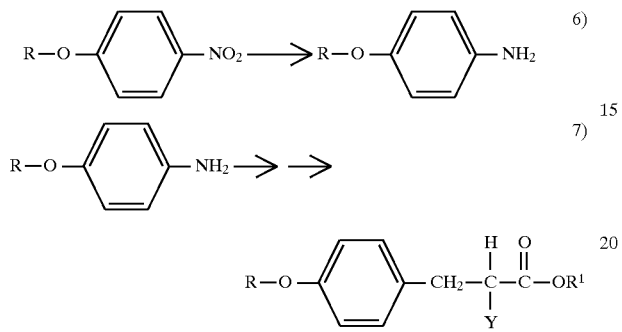

Where Y is a halogen.

The product of reaction 7) is then available for reaction with thiourea as previously described in reaction 3).

Reaction 5) is a condensation in the presence of sodium hydride. The reaction can be performed in a solvent such as dimethylformamide or tetrahydrofuran at −10° to 20° C. Subsequently, reaction 6) can be carried out, for example, by subjecting the product of reaction 5) to catalytic reduction with palladium carbon as a catalyst. The product of reaction 6) then undergoes the so-called Meerwin arylation. It is diazotized in the presence of a hydrohalic acid (HY) and then reacted with acrylic acid or an ester thereof in the presence of a copper catalyst, e.g. Cu(I) oxide, Cu(II) oxide, Cu(I) chloride or Cu(II) chloride.

B. Synthesis of Various Thiazolidine Derivatives Where $R_3$ is substituted by substituents represented by formulae IIb-d.

The following groups of compounds are each derivatives of the compound designated (I) above. The R group is variable and the synthesis of each will vary according to the chemical moieties desired.

1. Compound of formula IIa

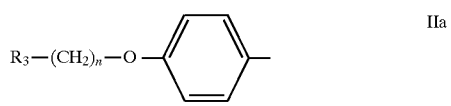

n is a methylene bridge of 1–4 carbons and $R_3$ is a compound of formula IIb, IIc or IId.

To provide compounds of formula IIa where $R_3$ is IIb, one may use the reaction sequence according to the method of Meguro et al., U.S. Pat. No. 4,812,570, which is incorporated herein by reference and consists of the following steps:

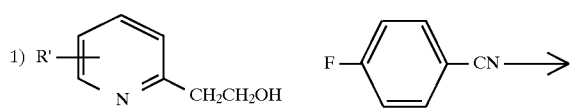

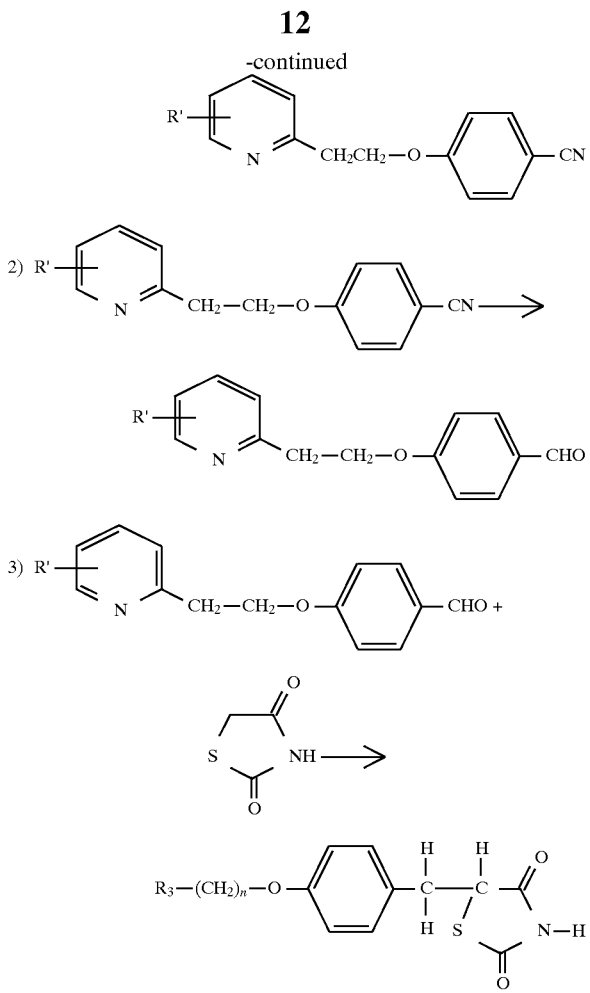

The specific conditions for the reaction sequence above involve first condensing the reactants of step 1) above in the presence of, for example, sodium hydride. The reaction is preferably conducted in a solvent such as dimethylformamide, dimethylsulfoxide, tetrahydrofuran or dimethoxyethane at −10° to 30° C.

The reaction step 2) is effected by heating the product of reaction 1) together with Raney nickel alloy in aqueous formic acid. The product of reaction 2) reacts with the thiazolidinedione ring in a suitable solvent-base system. Suitable solvents include short chain alcohols, dimethylformamide, dimethylsulfoxide, sulfolane, acetonitrile, dioxane, dimethoxyethane or acetic acid. Appropriate bases include ammonia, amines (for example, methylamine, ethylamine, n-butylamine, pyrrolidine, piperidine, morpholine, piperazine, diethylamine, diisopropylamine or triethylamine), sodium alkoxides (for example, sodium methoxide or sodium ethoxide), alkali metal carbonates, sodium hydroxide, sodium acetate, an so on. The thiazolidine ring compound is used in a proportion of 1 to 2.5 moles per mole of the product of reaction 2). The base is generally used in a proportion of 0.3 to 0.5 moles per mole of the product of reaction 2). This condensation reaction is generally conducted at 40° C. to reflux temperature and preferably at 60° to reflux temperature for 0.5 to 50 hours.

The thiazolidinedione ring reactant in step 3) is made according to the procedure detailed in part A above.

2. To provide compounds of formula IIa where R3 is IIc, one may use the reaction sequence according to the method of Kawamatsu et al., U.S. Pat. No. 4,461,902, which is herein incorporated by reference. The alpha-halocarboxylic acids used as starting materials in the production of the cyclohexyl-derivatized thiazolidines are synthesized by steps identical to those shown in reactions 5) through 7) above but where the compound reacting with p-nitrohalobenzene is:

In cases where the cyclohexane ring of the thus-obtained thiazolidine derivatives has a hydroxyl group substitution at one of the methylenes, such compounds may further be converted to those compounds which have an oxo group as a substituent on the cyclohexane ring by oxidation, while those compounds which have an oxo group on the cyclohexane ring may be converted to the corresponding hydroxyl compounds by reduction. Preferable oxidizing agents are of the chromium trioxide species (e.g. Jones' reagent, chromium trioxide-pyridine) and preferable reducing agents are sodium borohydride and aluminum isopropoxide-isopropanol.

3. To provide compounds of formula IIa where $R_3$ is IId,

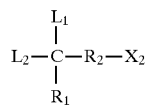

one may use the reaction sequence according to the method of Kawamatsu et al., U.S. Pat. No. 4,444,779, which is herein incorporated by reference. The reaction is as follows:

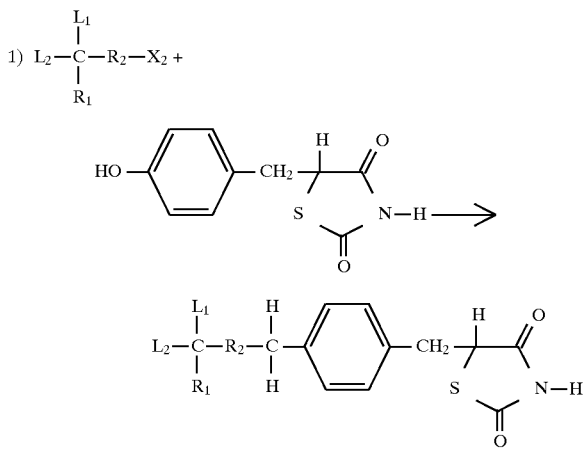

where the substituents are as defined earlier.

The above reaction will take place in the presence of a base such as sodium hydride, potassium carbonate, sodium carbonate, potassium hydroxide or sodium hydroxide in the presence of a solvent such as dimethylformamide or dimethylsulfoxide at 20° to 100° C.

C. The Synthesis of compounds of formula I where $R_1$ is substituted by radicals of formula IV.

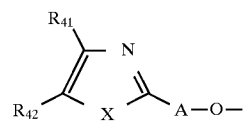

To obtain compounds of formula I where $R_1$ is substituted by radicals of formula IV, one may use the methods of synthesis detailed in the work of Meguro et al., U.S. Pat. No. 4,775,687, which is incorporated herein by reference. Two alternative methods are available.

First if the starting materials are conveniently available, the compound can be synthesized directly by the reaction:

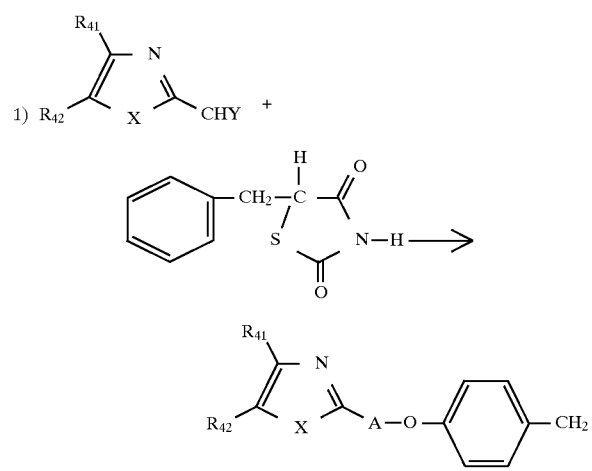

The above reaction is carried out in the presence of a base in an appropriate solvent. Examples of said base are sodium hydride, potassium hydride, sodium amide, sodium alkoxide (e.g. methoxide or ethoxide), potassium alkoxide (e.g. potassium t-butoxide) and potassium carbonate. Solvents include among others dimethylformamide, dimethylsulfoxide, sulfolane, tetrahydrofuran and dimethoxyethane. The reaction is preferably carried out by first allowing formation of a dianion by bringing such base into contact with the thiazolidine derivative in a molar ratio of 2:1 and thereafter adding the other reactant in an amount equimolar with the thiazolidine derivative. This condensation reaction is carried out preferably at 20° to 100° C. for 0.5 to 5.0 hours.

Alternatively, the starting compound containing the R group illustrated above (preferably where X is oxygen) can be produced by the following method:

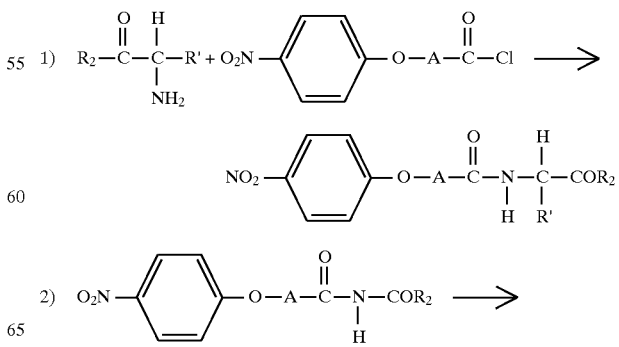

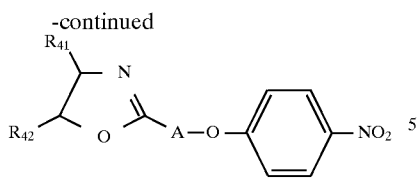

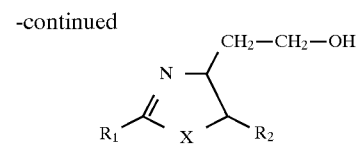

Where Y is a halogen of chlorine, bromine or iodine and $R_5$ is hydrogen or a lower alkyl.

These two reactions are followed by the series of steps previously detailed previously as steps 6) and 7) of part A. The product of reaction 7) is then available for reaction with thiourea as previously described.

Reaction 1) above is a condensation in the presence of a deacidifying agent (e.g. potassium carbonate, sodium carbonate, sodium bicarbonate, potassium bicarbonate, sodium hydroxide, potassium hydroxide or triethylamine) in a solvent such as dimethylformamide, dimethylsulfoxide, tetrahydrofuran, ethyl ether, ethyl acetate, chloroform or dichloromethane, or a mixed solvent prepared by adding water to such solvent as necessary at −10° to 50° C.

The product of reaction 1) is subjected to ring closure (reaction 2). This reaction is carried out in the presence of a dehydrating agent such as phosphorus oxychloride, thionyl chloride, phosphorus pentoxide, polyphosphoric acid, polyphosphoric acid esters, acetic anhydride or sulfuric acid, or mixtures of these. This reaction generally can be effected in an inert solvent (e.g. benzene, toluene, xylene, dichloromethane or chloroform) at about 30° to 140° C. or in an excess of dehydrating agent which serves also as a solvent within said temperature range. The dehydrating agent is used in an amount of 1–30 moles per mole of reactant.

D. The Synthesis of compounds of formula I where $R_1$ is substituted by radicals of formula V.

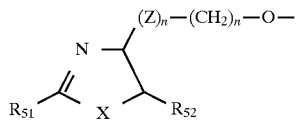

To obtain compounds of formula I where $R_1$ is substituted by radicals of formula V, one may use the methods of synthesis detailed in the work Meguro et al., U.S. Pat. No. 4,725,610, which is incorporated herein by reference. The steps of the synthesis of the starting compound are as follows:

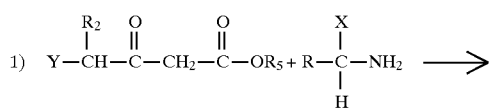

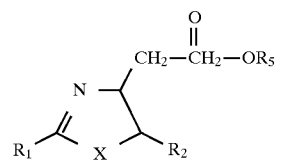

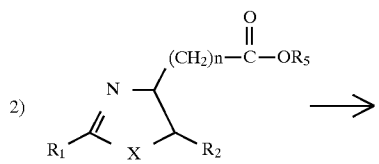

The product of either reaction 1) or 2) above may be used as a reactant either in the sequence of steps detailed earlier as 5) through 7) or, alternatively, through reaction sequence 1) through 3) as described for Compound 1 to produce the derivatized thiazolidine.

Reaction 1) above is easily conducted in a alcohol solvent such as methanol, ethanol, propanol, etc. or without a solvent by heating to about 40° to 150° C.

The product of reaction 1) is reduced in a conventional method, for example, using lithium aluminum hydride.

E. The Synthesis of compounds of formula I where $R_1$ is substituted by radicals of formula VI.

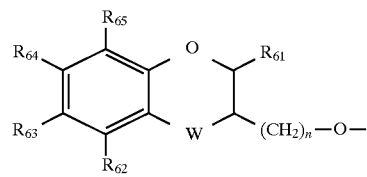

To obtain compounds of formula I where $R_1$ is substituted by radicals of formula VI, one may use the methods of synthesis detailed in the work of Yoshioka et al., U.S. Pat. No. 4,572,912, which is incorporated herein by reference. Yoshioka provides two alternative methods to generate the compounds of this family.

Method A—(If the starting compound is available):

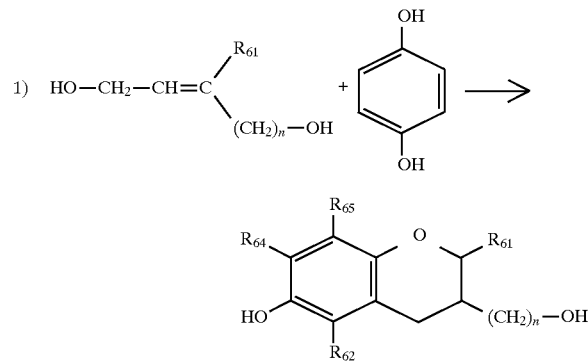

as described in West German Patent No. 3,010,504, in the presence of aluminum chloride. The product of this reaction is then taken through the steps detailed earlier as reactions 5) through 7).

Method B—(If the starting compound is available):

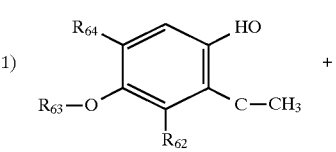

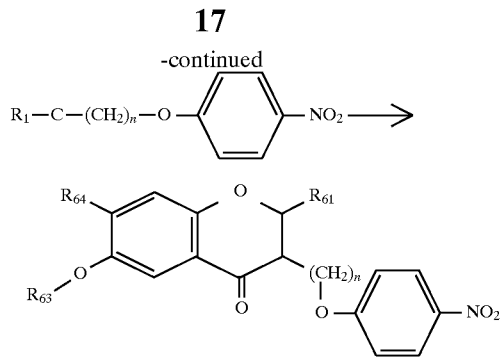

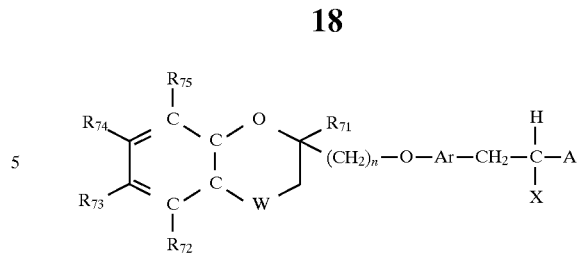

The acetophenone derivative reactant above may be prepared, for example, as described in Chem. Berichte, 95, 1413-. The other starting compound, p-nitrophenoxyalkyl alkyl ketones, may be prepared, for example, as described in J. Med. Chem., 21, 386-(1978). The reaction takes place in the presence of a secondary amine and preferably in a suitable solvent which may include aliphatic and aromatic hydrocarbons such as petroleum ether, benzene, toluene, xylene, hexane or cyclohexane; halogenated aliphatic and aromatic hydrocarbons such as carbon tetrachloride, methylene chloride, chloroform, chloro- and dichlorobenzene; ethers such as diethyl ether, tetrahydrofuran and dioxane; amides such as dimethylformamide, dimethylacetamide and N-methylpyrrolidone; alcohols such as methanol, ethanol and ethylene glycol monomethyl ether; esters such as ethyl acetate; nitriles such as acetonitrile; and sulfoxides such as dimethylsulfoxide.

Examples of preferable secondary amine catalysts include diethylamine, dimethylamine, N-methylpiperazine, pyrrolidine, piperidine or morpholine, of which pyrrolidine is particularly preferred.

The molar ratio of reactants is not particularly critical, but to avoid waste roughly equimolar amounts are used. The amount of secondary amine is preferably from 0.1 to 1.0 mole per mole of reactant.

In general it is preferred to carry out the reaction at a temperature of from 10° to 120° C. for a period from 30 minutes to three days.

Formulations of compound VI in which W is hydroxy substituted methylene, >C—OH, may be prepared by reducing the corresponding compound in which W is oxy substitute methylene, >C=O.

The reducing agent for this reaction is any one which is capable of reducing a ring carbonyl group to a hydroxy group without affecting the remainder of the molecule. Suitable reducing agents include borohydrides, especially sodium borohydride. Preferably one employs an excess of reductant of from one to 20 moles per mole of the other reactant. The reaction is preferably carried out at 0° to 100° for from one to twenty hours.

F. The Synthesis of compounds of formula I where $R_1$ is substituted by radicals of formula VII.

To obtain compounds of formula I where $R_1$ is substituted by radicals of formula VII, one may use the methods of synthesis detailed in the work of Horikoshi et al., EPO 0277836, which is herein incorporated by reference.

One means of synthesizing thiazolidine derivatives containing the structure depicted above entails the direct reaction of where X represents a halogen and A represents cyano, carboxy, or $C_2$–$C_6$ alkoxycarbonyl with thiourea analogously to steps 3) and 4) in Part A. Where such a starting compound is unavailable, it may be synthesized according to the method of Horikoshi et al., EPO 0277836, and as presented below.

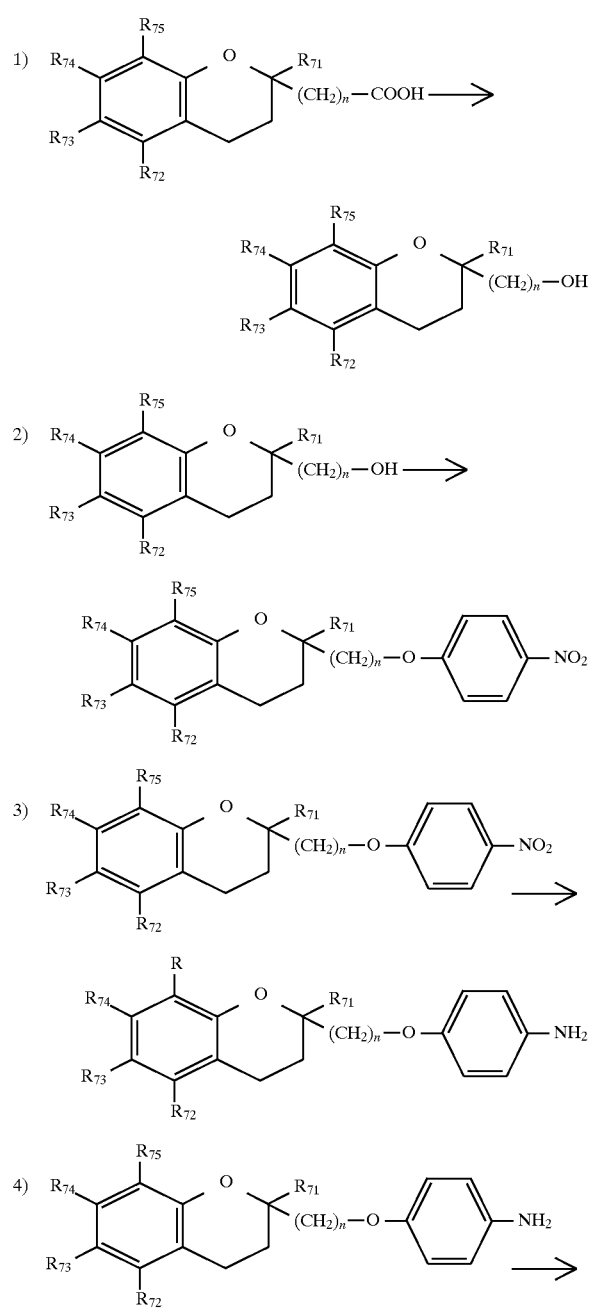

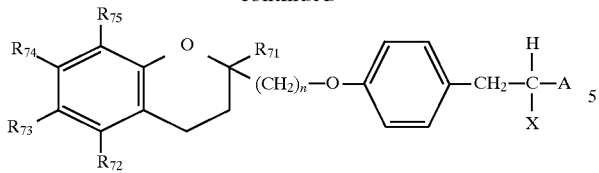
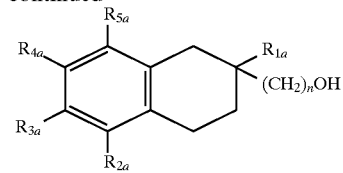

Reaction 2) involves the same chemistry as reaction 5) of the process depicted in Part A.

In step 2) it is preferred that any free hydroxy group which is a ring substituent be protected. Examples of suitable protecting groups include optionally substituted alkyl groups such as methoxymethyl and 2-tetrahydropyranyl groups.

In step 3) it is preferred to protect any amino group with suitable protecting groups including alkoxycarbonyl groups, such as methoxycarbonyl or ethoxycarbonyl groups.

In addition when synthesizing the product of reaction 3), if the product of reaction 2) is substituted by a hydroxy group protected by any one of the alkyl groups mentioned above or is substituted by a hydroxy-containing group protected by any one of the alkyl groups mentioned above, the protected group may be removed and the resulting hydroxy group may be protected again with another group, for example, an acyl group, such as an acetyl or benzoyl group.

Step 3) is a reduction of the product of step 2); a similar reaction may be carried out to convert nitro substituents on these compounds to amino groups which can then be protected as mentioned above.

The reduction steps, 1) and 3), may be a catalytic reduction process employing hydrogen or reduction with a metal, such as zinc or iron, and an acid (which may be a mineral acid, such as hydrochloric acid or sulfuric acid, or an organic acid, such as acetic acid. The preferred catalyst is palladium on carbon, Raney nickel or platinum oxide. The hydrogen pressure is preferably from one to six atmospheres (1.01 to 6.06 bars). The reaction is preferably conducted in a solvent having no adverse effect on the reaction. Examples of suitable solvents include alcohols, such as methanol or ethanol; aromatic hydrocarbons such as benzene or toluene; organic acids such as acetic acid; amides such as dimethylformamide; water; or a mixture of any two or more of the above.

The reaction conditions may vary depending on the chemical nature of the starting material, the method employed for reduction or the solvent, but is normally effected at 20° to 50° C. for from several minutes to 50 hours.

Reaction 4) is the same process detailed above as an alternative method for generating compound (I). See step 7).

If unavailable, the starting compound for step 1) above may be synthesized beginning with a phenol in the following reaction:

5) 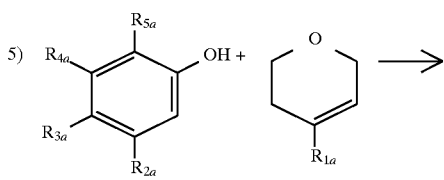

This reaction generates the same product as that of step 1) above. The reaction conditions are described in Japanese Patent Application Kokai No. 201775/83.

G. The Synthesis of compounds of formula I where $R_1$ is substituted by radicals of formula VIII.

To obtain compounds of formula I where $R_1$ is substituted by radicals of formula VIII,

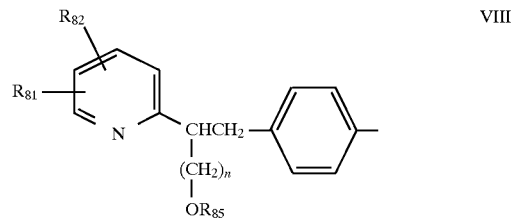

VIII one may use the methods of synthesis detailed in the work of Meguro et al., U.S. Pat. No. 4,582,839, which is incorporated herein by reference. Starting with a compound illustrated as:

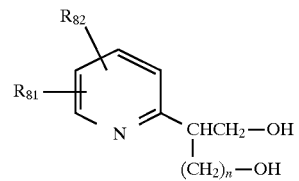

it is taken through an analogous reaction sequence detailed earlier as steps 5), 6) and 7) for the production of compound (I). At this point the product of reaction 7) will be

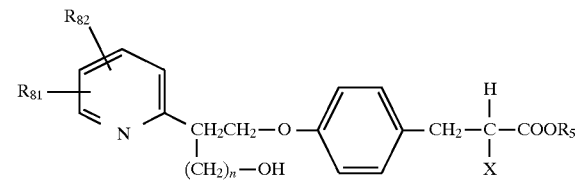

where R' is a lower alkyl of 1 to 4 carbons and said ester can be can be acylated by the following reaction:

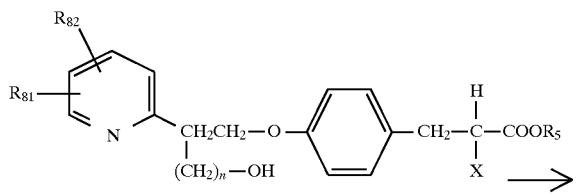

-continued

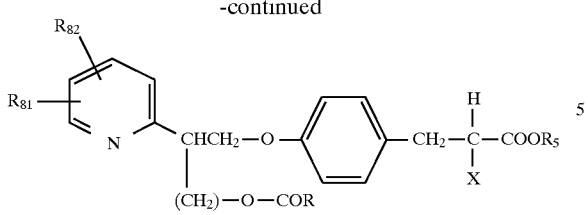

This acylation is easily conducted by heating with an acid halide or acid anhydride 80° to 150° C.

This product is then available to react with thiourea as previously described to form the thiazolidine derivative.

H. The Synthesis of compounds of formula I where $R_1$ is substituted by radicals of formula IX.

To obtain compounds of formula I where $R_1$ is substituted by radicals of formula IX, one may use the methods of synthesis detailed in the work of Meguro et al., U.S. Pat. No. 4,486,594

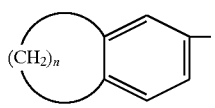

IX which is incorporated herein by reference. Starting with a compound illustrated as:

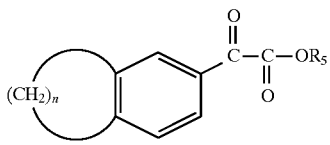

where $R_5$ is a lower alkyl of 1–4 carbons and proceeding analogously through the steps 1) through 3) as detailed for the compounds of formula I described above in part A.

I. The Synthesis of compounds of formula I where $R_1$ is further substituted by radicals of formula XI.

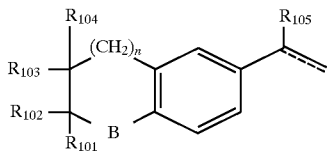

XI

The compounds of formula XI are prepared, for example by the method illustrated below as detailed in the work of Eggler, et al., U.S. Pat. No. 4,703,052 which is incorporated herein by reference.

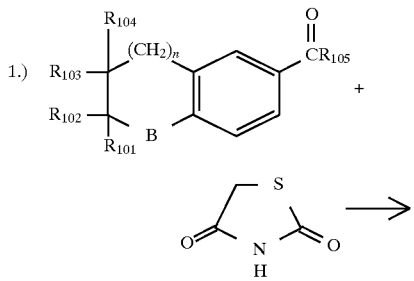

-continued

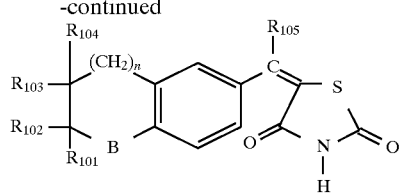

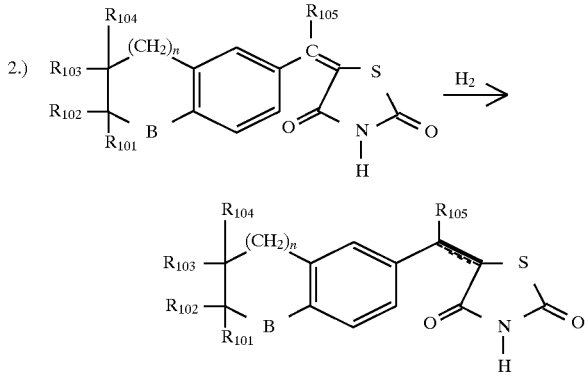

In the first step of the above synthetic scheme, approximately equimolar amounts of the carbonyl reactant and the thiazolidinedione are heated in the presence of a mild base to provide the olefin product. While this step may be carried out in the presence of a reaction-inert solvent, it is preferably carried out in the absence of solvent at a temperature which is sufficiently high to cause at least partial melting of the reaction mixture. A preferred such temperature is in the range of from 100° to 250° C. and especially preferred is a temperature of from 140° to 200° C.

Examples of suitable mild bases for the above reaction include the alkali metal and alkaline earth salts of weak acids such as the ($C_1$–$C_{12}$) alkyl carboxylic acids and benzoic acid; alkali metal and alkaline earth carbonates and bicarbonates such as calcium carbonate, magnesium carbonate, potassium bicarbonate; and tertiary amines such as pyridine, N-methylmorpholine, N-ethylpiperidine and the like. An especially preferred mild base is sodium acetate for reasons of economy and efficiency.

In a typical such reaction the aldehyde or ketone starting material and thiazolidinedione are combined in approximately equimolar amounts with a molar excess, preferably a 2–4 fold molar excess, of anydrous sodium acetate and the mixture is heated at a temperature high enough to effect melting, at which temperature the reaction is substantially complete in from about 5 to 60 minutes. The desired olefin is then isolated, for example, by mixing with water and filtration, to obtain the crude product, which is purified, if desired, e.g., by crystallization or by standard chromatographic methods.

The olefinic product of step 1 serves as intermediate for preparation of the corresponding reduced compound shown as the product of step 2. The reduction of the above olefin may be carried out by employing a wide variety of reducing agents which are known to reduce carbon-carbon double bonds. However, since hydrogenation methods have a well-known tendency to cleave benzylic carbon-oxygen bonds a preferred method for reduction of the compounds of the olefin is conventional sodium amalgam reduction in methanol, usually at or about ambient temperature.

When the reduction is substantially complete, the desired product of formula XI is then isolated by filtration, the solvent evaporated and the product purified, if desired, by well known methods such as crystallization or by chromatography.

The reactions employed to prepare the compounds of this invention can generally be monitored by standard TLC methods, employing commercially available plates. Suitable eluants are common solvents such as chloroform, ethyl acetate or hexane or suitable combinations thereof which will differentiate starting materials, products, by-products, and in some cases intermediates. Applying these methods, which are well-known in the art, will permit further improvement in the methodology of selection of more optimal reaction times and temperatures.

The requisite 2,3-dihydrobenzofurans, 2,3-dihydrobenzothiophenes, chromans, thiochromans, tetrahydrobenzooxepins and tetrahydrobenzothiepins, as well as the corresponding bromo-substituted and hydroxyalkyl-substituted compounds which are precursors of the starting aldehydes and ketones of are prepared by a variety of methods known in the art. A process for preparing one simple aldehyde is illustrated below. The preparation of other aldehydes can be found in U.S. Pat. No. 4,703,052, Examples 1–9 which is incorporated by reference herein.

General Method for Preparation of Aldehyde Starting Compounds

5-Formyl-2,3-dihydrobenzofuran

A solution of 9.4 ml (83.4 mmole) 2,3-dihydrobenzofuran in 250 ml methylene dichloride was cooled under nitrogen to 0° to –5° C. and 18 ml (167 mmole)titanium tetrachloride was added dropwise at 0° C. The resulting brown mixture was stirred 10 minutes and 8.3 ml (91.6 mmole) 1,1-dichloromethyl methylether was then added dropwise at 0° C. During this addition the reaction mixture became dark red. The mixture was allowed to warm to room temperature, stirred for two hours and poured slowly into a 2 liter beaker containing 700 ml saturated aqueous sodium bicarbonate solution. The resulting mixture was filtered through diatomaceous earth and the solids washed with methylene dichloride. The separated organic layer was dried ($Na_2SO_4$) and the solvent evaporated to afford a residual oil, log (81%) of which appeared homogeneous on silica gel TLC, eluting with an ethyl acetate/hexane/5% acetic acid 1:5:5 by volume. Mass spectrum (m/e): 148 (M+), 147, 119.

Therapeutic Administration

Various compositions of the present invention are presented for administration to humans and animals in unit dosage forms, such as tablets, capsules, pills, powders, granules, eye drops, oral solutions or suspensions and water-in-oil emulsions containing suitable quantities or formulations of thiazolidine derivatives.

For oral administration, either solid or fluid unit dosage forms can be prepared. For preparing solid compositions such as tablets, thiazolidine derivatives are mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the thiazolidine compound with an inert pharmaceutical diluent and filling the mixture into a hard gelatin capsule of appropriate size. Soft gelatin capsules are prepared by machine encapsulation of a slurry of the thiazolidine compound with an acceptable vegetable oil, light liquid petrolatum or other inert oil.

Fluid unit dosage forms for oral administration such as syrups, elixirs and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

Examples of suitable unit dosage forms in accord with this invention are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

The route of administration can be oral, rectal, transdermal, nasal or by parenteral injection. Oral administration is preferred. An effective quantity of thiazolidine derivative is employed in treatment. The dosage of the specific compound for treatment depends on many factors that are well known to those skilled in the art. They include for example, the route of administration and the potency of the particular compound. A dosage schedule for humans of about 80 kgs. is from about 1 microgram to 5 grams of compound in a single dose. More specifically, the single dose is about 2 grams of compound. More specifically the single oral dose is about 1–10 milligrams of compound. Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLES

Example 1. Evidence that thiazolidine pharmaceuticals having antiinsulin activity will also control essential hypertension.

Two groups of six week old obese Zucker rats were purchased from Charles River Laboratories. Previous studies have documented that these rats are characterized by hypertension, insulin resistance and hyperinsulinemia. In the experimental group ciglitazone was added to the diet (0.05% w/w). The control group was given the same diet without ciglitazone. The rats were individually housed in metabolic cages and daily food intakes were measured for each rat. Twenty four hour urine collections were obtained for measurements of urine output. The amount of ciglitazone ingested by the experimental group was 33 to 58 mg/kg body weight per day over the duration of the study.

After four weeks mean arterial pressures were measured in the unanaesthetized, unrestrained state through indwelling femoral arterial catheters. To measure blood pressure the femoral catheter was connected via an extension catheter (P.E. 50) to a low volume pressure transducer (model P50, Gould Inc., Cleveland, Ohio). the measurement of the blood pressure was begun 30 to 60 minutes after connecting the catheter to the transducer. The output of the transducer was sent to a Gould transducer preamplifier and the mean arterial pressure signal passed to an analog-digital (A/D) converter (DASH-8, Metabyte Co., Taunton Mass.) installed in an IBM AT microcomputer. Data acquisition software (Labtech Notebook, Laboratory Technologies Co., Wilmington, Mass.) was employed to sample the blood pressure signal every 15 seconds over a period of two hours. The average of these 480 measurements obtained over the two hour interval was then calculated to yield each animal's mean arterial pressure. (Hypertension, 13:896–901, 1989).

Mean arterial pressure in the rats given ciglitazone was significantly lower than that in the untreated control rats (Table 1). In the rats given ciglitazone, the decreased blood pressure was associated with a significantly decreased plasma concentration of insulin, approximately half that of control rats. There was a statistically significant direct correlation between the plasma concentration of insulin and blood pressure (r=0.56, p=0.014) (FIG. 2). In the rats given ciglitazone, urine output was significantly increased. In the rats given ciglitazone, mean body weights and food intakes (measured weekly) were not different from control rats.

TABLE 1

Effect of Ciglitazone on Mean Arterial Pressure (MAP), Plasma Insulin Concentration and Urine Output*

| Measurement | Control (n = 9)*** | Ciglitazone (n = 6)*** | Significance** |
|---|---|---|---|
| MAP (mm Hg) | 119 ± 2 | 112 ± 4 | p < 0.05 |
| Plasma insulin | 161 ± 19 | 72 ± 6 | p < 0.001 |
| Urine output (ml/wk) | 80 ± 5 | 97 ± 8 | p < 0.05*** |

*The data are presented as the mean + SEM of n determinations
**Significance was determined by Student's t-test
***Because of complications during surgery, one animal was lost from the control group, and four from the experimental group.

Example 2. Treating patients having essential hypertension with an effective amount of thiazolidine derived agents.

In a 25 year old male patient of 80 kilograms exhibiting moderate hypertension of 140/90 to 160/110, an oral dose of an alginate/cellulose/stearate based tablet having 5 mg of a thiazolidine derivative is administrated on a daily basis until the blood pressure lowered to acceptable averages of about 135/85.

What is claimed is:

1. A method for controlling essential hypertension and its related cardiovascular syndrome in a mammal host in need thereof comprising administering an effective amount of the thiazolidine derivative 5-(4-[2-(5-ethyl-2-pyridylethoxy]benzyl)-2,4-thiazolidine dione.

* * * * *